United States Patent [19]

Adams

[11] 4,335,620
[45] Jun. 22, 1982

[54] TEMPERATURE CONTROLLED SAMPLE CARRIER

[75] Inventor: Wade J. Adams, Kalamazoo, Mich.

[73] Assignee: The Upjohn Company, Kalamazoo, Mich.

[21] Appl. No.: 169,327

[22] Filed: Jul. 16, 1980

[51] Int. Cl.³ ............................................ G01N 35/04
[52] U.S. Cl. .................................... 73/863.11; 422/64
[58] Field of Search .......... 73/423 A, 863.11, 864.91; 422/62, 63, 64, 65, 67, 81, 82, 99, 100, 102

[56] References Cited

U.S. PATENT DOCUMENTS

| | | | |
|---|---|---|---|
| 2,418,254 | 4/1947 | Fleharty | 219/39 |
| 3,546,946 | 12/1970 | Smith | 73/423 |
| 3,764,268 | 10/1973 | Kosowsky et al. | 422/64 |
| 3,790,346 | 2/1974 | Ritchie | 23/253 |
| 3,832,135 | 8/1974 | Drozdowski et al. | 73/423 A |
| 3,873,273 | 3/1975 | Moran et al. | 422/64 |
| 3,918,913 | 11/1975 | Stevenson et al. | 23/259 |
| 3,960,003 | 6/1976 | Beyer et al. | 73/61.1 C |
| 3,969,079 | 7/1976 | Catarious et al. | 422/64 |
| 4,054,416 | 10/1977 | Duff | 422/64 |
| 4,113,437 | 9/1978 | Duff et al. | 422/63 |

Primary Examiner—S. Clement Swisher
Attorney, Agent, or Firm—Blanchard, Flynn, Thiel, Boutell & Tanis

[57] ABSTRACT

A temperature controlled sample carrier, usable in liquid chromatography apparatus, includes a rotating sample rack having a circumferential array of upward facing sample holes adjacent its periphery for receiving sample vials and orbiting same sequentially past a sampling station. The rack is a solid cylindrical block of heat conducting material which forms a massive heat sink. An insulative cup receives the sample block and rotates therewith. A temperature control device carries a controlled temperature fluid in heat conductive contact with the central portion of the sample block and is overlaid by an insulative cover device which rotates with the block. An insulative cover ring is fixed with respect to the sampling station, overlies the array of sample holes in the block, and extends between the peripheral wall of the cup and the cover device. A circumferentially narrow opening in the cover ring permits access by a sampling device at the sampling station to the upper ends of sequentially presented sample vials rotating therepast with the sample block.

14 Claims, 7 Drawing Figures

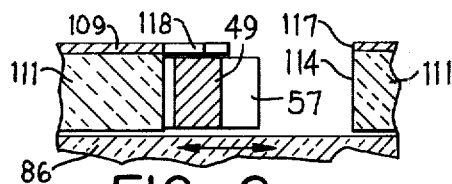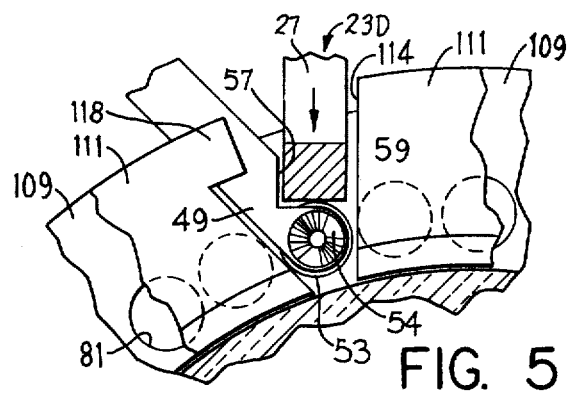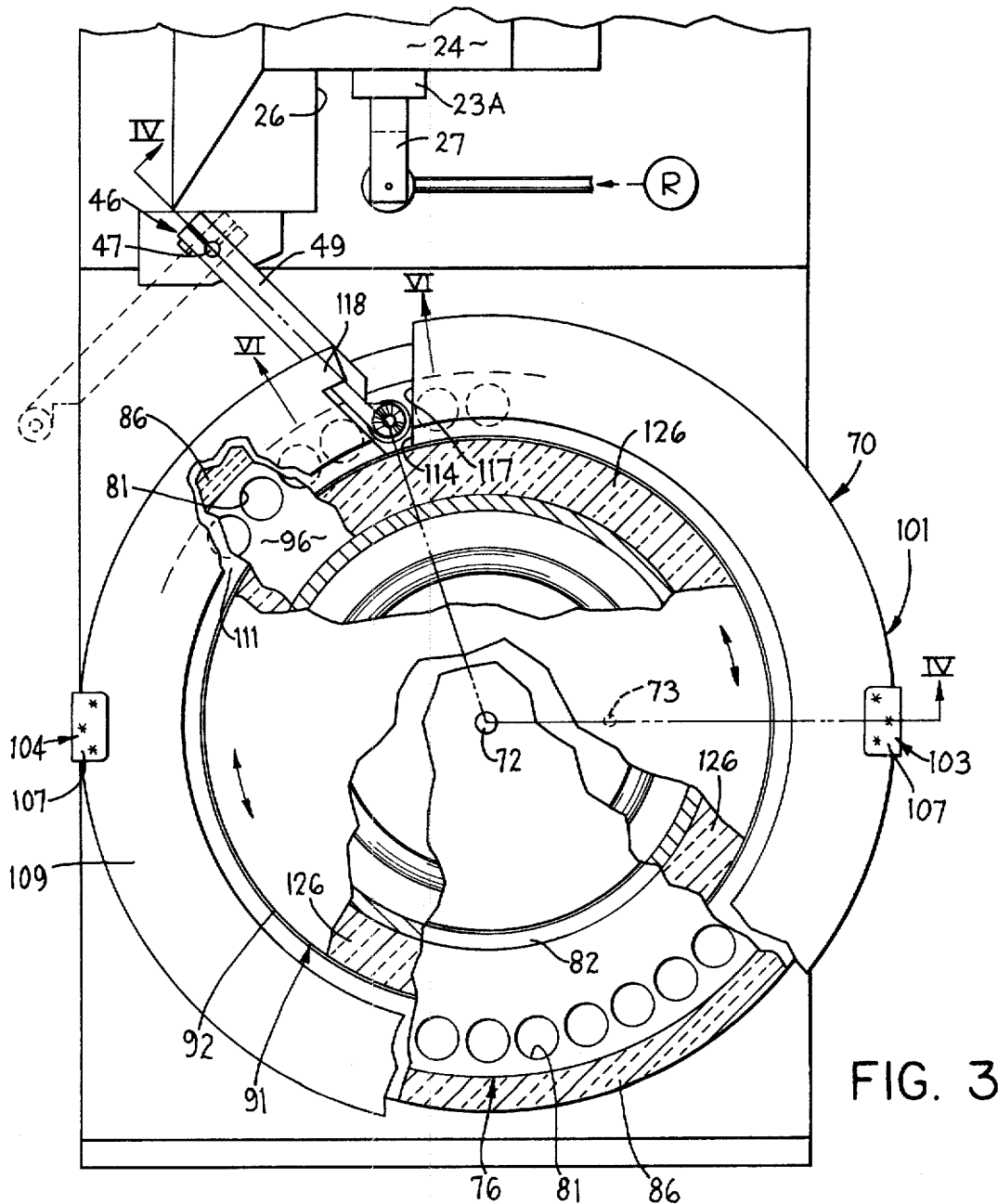

TEMPERATURE CONTROLLED SAMPLE CARRIER

FIELD OF THE INVENTION

This invention relates to a temperature controlled sample carrier apparatus and more particularly to such an apparatus capable of controlling temperatures of samples in an automatic sampler in a high performance liquid chromatography apparatus.

BACKGROUND OF THE INVENTION

The temperature controlled sample carrier apparatus of the present invention was developed in connection with the automatic sampler of an automated high performance liquid chromatography apparatus and for purposes of convenience will be disclosed in this environment. It will be understood that the present invention, at least in its broader aspects, may be applied to other types of apparatus in which successive samples are to be moved relative to a work station while maintaining control of the temperature of the samples.

High performance liquid chromatography (HPLC) has gained widespread use in the past decade as a highly specific and sensitive analytic method. The use of HPLC in situations where large numbers of samples must be analyzed (e.g. quality control, pharmacokinetic and clinical laboratories) is also desirable because of the relative ease of sample preparation and the rapidity of sample analysis.

U.S. Pat. No. 3,960,003 (Beyer et al) discloses such a liquid chromatography apparatus.

To permit rapid processing of large numbers of samples in sequence automatically, an automatic sampler has been used in such liquid chromatography apparatus. Typically, the automatic sampler includes a rack carrying a circumferential array of samples and is rotatably stepped to successively present samples to a probe at a sampling station, the probe being connected to the chromatography apparatus for injection of successive samples thereinto. As set forth in the aforementioned Beyer patent, a suitable automatic sampler is that disclosed in U.S. Pat. No. 3,546,946 (Smith).

While liquid chromatographs incorporating automatic samplers for unattended injection of samples are commercially available, none is known which permits close temperature control of the samples.

Previous automatic samplers could not be used with thermally labile samples, i.e. samples which break down or undergo change upon deviation from certain temperature conditions. Accordingly, such thermally labile liquid samples were tested by hand on a one-at-a-time basis. Also, for certain solids of a type tending to degrade after a period of time in solution and wherein instability of the sample may be affected by temperature, it has been common to dissolve one sample at a time in a solvent and immediately carry out chromatographic testing of the dissolved sample before degradation could occur or be accelerated by temperature changes.

Prior automatic samplers also were not previously used in kinetic (rate of reaction) studies where temperature control is necessary during the reaction.

Prior rotating sample transports, not of the aforementioned Smith type and not necessarily suitable for chromatographic samples, have proposed generally temperature related features.

For example, U.S. Pat. No. 3,790,346 (Ritchie) discloses a testing apparatus for automatically determining prothromben times. Here, however, a single, fixed heating station is provided past which successive blood plasma samples are rotated, the heating station being flanked by first and second reagent adding stations. Thus, the purpose is to elevate the temperature of the samples sequentially, rather than to maintain temperature control of all samples simultaneously.

U.S. Pat. No. 2,418,254 (Fleharty) and U.S. Pat. No. 4,113,437 (Duff) rely on direct contact between plural sample vials and a circulating fluid, the temperature of which is intended to be controlled. However, neither of these patents is directed to chromatographic sample handling devices and both are complicated by need for a common fluid contact space for the vials, means for sealing against leakage of fluid therefrom, and vials suitable for contacting such fluid, as well as the need both for bringing of temperature controlling fluid into the container from an outside source and arrangements for circulating of the same or a different temperature controlling fluid among the vials. Moreover, problems of temperature stratification and/or uneven circulation of temperature control fluid among the vials may arise. Also, the vials are either not readily replaceable in the apparatus or have parts continuously exposed in heat exchange relation with the atmosphere.

Thus, the objects of this invention include provision of:

1. An apparatus for maintaining temperature control in a sample carrier apparatus, particularly of a type usable in the automatic sampler of an automatic high performance liquid chromatography system.

2. An apparatus, as aforesaid, capable of simultaneously maintaining a plurality of samples at a preselected temperature within close tolerances, and wherein the temperature is preselectable from a wide temperature range extending both above and below normal room temperature.

3. An apparatus, as aforesaid, capable of maintaining plural samples at a preselected constant temperature during storage remote from an automatic sampler, during installation of the sample carrier on and removal of the sample carrier from an automatic sampler, as well as during sampling in an automatic sampler.

4. An apparatus, as aforesaid, which permits rapid heat exchange between samples on the sample carrier but blocks rapid heat exchange of such samples with the surrounding atmosphere, and which substantially insulatively encloses the particular sample vial then being sampled and fully insulatively encloses the remaining sample vials on the carrier.

Other objects and purposes of this invention will be apparent to persons acquainted with apparatus of this general type upon reading the following specification and inspecting the accompanying drawings.

The objects and purposes of this invention are met by providing a temperature controlled sample carrier usable in liquid chromatography apparatus, and including a rotating sample rack having a circumferential array of upward facing sample holes adjacent the periphery for receiving sample vials and orbiting same sequentially past a sampling station. The rack is a solid cylindrical block of heat conducting material which forms a massive heat sink. An insulative cup receives the sample block and rotates therewith. A temperature control device carries a controlled temperature fluid in heat conductive contact with the central portion of the sample block and is overlaid by an insulative cover device which rotates with the block. An insulative cover ring is fixed with respect to the sampling station, overlies the array of sample holes in the block, and extends between a peripheral wall of the cup and cover device. A circumferentially narrow opening in the cover ring permits a sampling device at the sampling station access to the upper ends of sequentially presented sample vials rotating therepast with the sample block.

BRIEF DESCRIPTION OF THE DRAWINGS

FIG. 3 is an enlarged, fragmentary, partially broken top view of the apparatus of FIG. 2.

FIG. 5 is an enlarged fragment of FIG. 3 showing the probe carriage of the automatic sampler in sampling position adjacent the sampling needle guide.

FIG. 6 is an enlarged fragmentary cross-sectional view substantially taken on the line VI—VI of FIG. 3.

DETAILED DESCRIPTION

Figure 1:
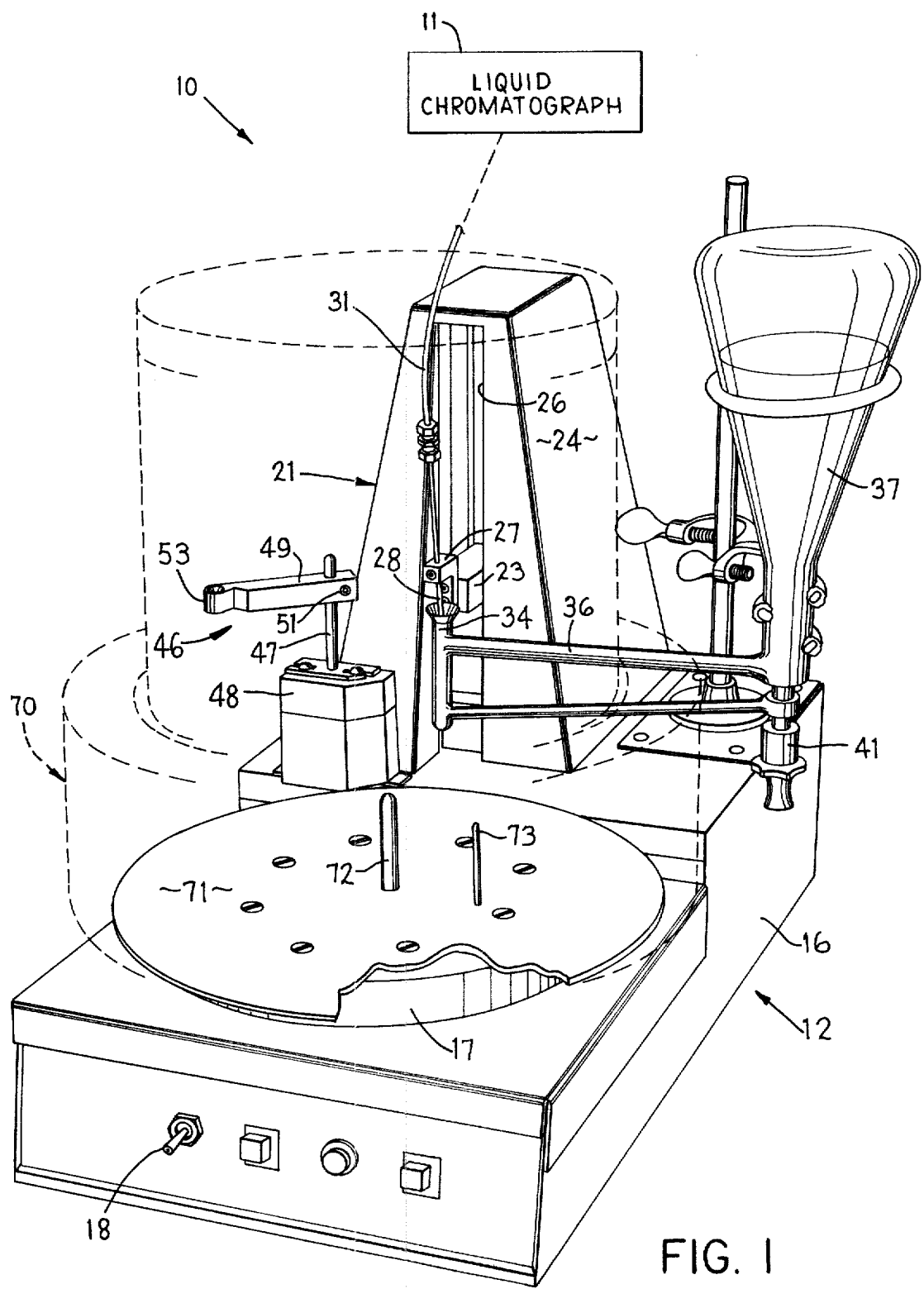
FIG. 1 is a pictorial, partially schematic view of a liquid chromatograph apparatus equipped with an automatic sampler of a type with which a temperature controlled sample carrier of the present invention is usable.

To facilitate disclosure of a preferred embodiment of the invention, FIG. 1 shows an automatic liquid chromatography apparatus 10 including a liquid chromatograph 11 to which successive samples to be tested are fed by an automatic sampler 12. The automatic liquid chromatography apparatus may be of the type shown in U.S. Pat. No. 3,960,003 (Beyer) and the automatic sampler 12 may be of the type shown in U.S. Pat. No. 3,546,946 (Smith), to which reference may be made for further details of structure and operation of a suitable sampler and liquid chromatography apparatus as a whole.

However, the structure of the automatic sampler 12 of FIG. 1 is briefly summarized below. The sampler 12 includes a base 16. A turntable 17 extends above the front portion of the base 16 and is supported thereon by any convenient means (not shown) for stepwise rotation by a suitable motor, schematically indicated at M in FIG. 4. A front panel control switch 18 selects forward, reverse or off conditions of the motor M and hence of turntable 17.

Conventionally, the turntable 17 supports an open sample rack (not here shown) of the type disclosed in the aforementioned Beyer or Smith patents for rotationally stepwise presentation of successive, circumferentially distributed samples to a sampling station 21 fixed on the rear part of base 16. A probe carriage 23 is housed in an upstanding housing 24 on the rear portion of base 16 and extends forward through an upstanding front opening slot 26 in the housing. An inverted L-shaped bracket 27 on the carriage supports an upstanding, downwardly opening probe 28 connected at its upper end through a flexible tube 31 to the sample input of the liquid chromatograph 11. The probe 28 is a conventional hollow needle probe.

A rinse liquid receptacle 34 is fixed in front of the slot 26 to receive the lower end of the probe 28. The receptacle 34 connects through a supply conduit 36 to a rinse liquid source 37 having a drain valve 41. The supply conduit 36 maintains a desired level of rinse liquid in the receptacle 34.

Figure 2:
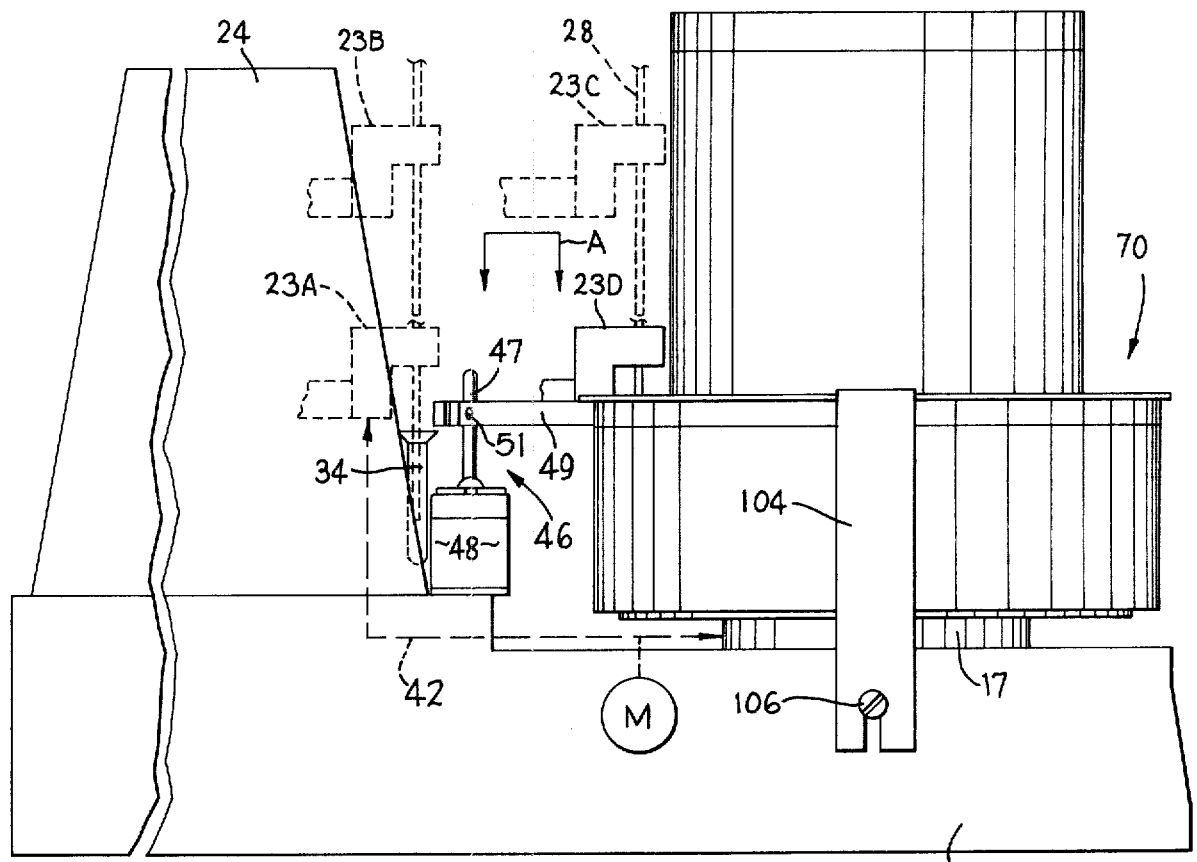
FIG. 2 is a side elevational view of the FIG. 1 apparatus including a temperature controlled sample carrier.

The probe carriage 23 is supported in the housing 24, by any convenient means (not shown), for movement in a vertical plane through a substantially inverted U-shaped path, indicated by the double-ended arrow A in FIG. 2. Thus, the probe is movable from a rear, rinse liquid obtaining position 23A upward to a rear disengaged position 23B, thence forwardly to a front disengaged position 23C and then down to a front sampling position 23D whereafter probe movement is reversed to return the probe along the same inverted U-shaped path to rinse position 23A. Suitable synchronous drive means (not shown but schematically indicated by the broken line 42 in FIG. 2) cause the motor M to synchronously drive the probe 23 and turntable 17, such that for each angular step of the turntable 17, the probe 23 completes one cycle through its path A. More particularly, after the probe moves from its sampling position 23D to position 23C, the turntable 17 is free to begin a circumferential step, which step is to be completed by the time that the probe 23 moves from position 23C through position 23B to rinse position 23A and then back through position 23B to position 23C, the turntable 17 being once again stopped as the probe 23C moves down to its forward lower sampling position 23D.

The apparatus above described thus corresponds to that disclosed in more detail in the aforementioned Beyer and Smith patents.

A sampling needle guide unit 46 (FIGS. 1 and 2) comprises an upstanding rod 47 fixed atop the base 16 by a support 48 between the housing 24 and turntable 17. A cantilevered guide arm 49 is provided with a substantially keyhole-shaped slot in its rear end through which it receives the rod 47. By release of a set screw 51 thereon, the arm 49 can be adjusted pivotally and vertically on the rod 47 and hence swung into a probe guiding position immediately beneath the sampling position 23D of the probe carriage (in FIG. 2) or can be swung away from the turntable to the out-of-the-way, nonoperating position in FIG. 1. The front end 53 of the guide arm 49 is rounded (FIG. 1) and provided with a funnel-shaped vertical guide opening 54 (FIG. 4) to precisely guide the lower input tip 56 of the probe 28 as it moves downward into its sampling position. As seen in FIG. 5, the arm 49 has a V-shaped notch 57 at the rear side of the guide opening 54 to permit closer positioning of the vertical leg 59 of the L-shaped probe bracket 27.

Turning now more particularly to the sample temperature control aspect of the invention, a temperature controlled sample carrier 70 (FIGS. 2-4) includes a base plate 71 overhanging and fixed as by screws coaxially on turntable 17. The turntable 17 fixedly carries a coaxial center pin 72 and eccentrically located key pin 73, which extend upwardly through openings in the base plate 71.

A disk of insulation material 74 rests atop the base plate 71 and receives the pins 72 and 73 upward through holes therein. The disk and base plate are preferably circular and of substantially the same diameter.

A solid block 76 of highly heat-conductive material, such as aluminum, serves both as a rack for supporting a plurality of sample vials and as a heat sink to assist in controlling the temperature of such vials. In the preferred embodiment shown, the block 76 takes substantially the form of a right circular cylinder of aluminum coaxially supported on and coextensive in diameter with the insulative disk 74. Coaxial and eccentric openings in the bottom of the block 76 respectively receive the center pin 72 and key pin 73 upward thereinto for maintaining the block 76 centered on the supporting disk 74 and base plate 71 and for stepwise rotational driving of the block 76, respectively. At least the key pin hole 78 in the block 76 is blind.

The top face 79 of the block 76 has a circumferential array of sample vial recesses, or holes, 81 and, in the preferred embodiment shown, an annular locating groove 82 spaced radially inward from the array of holes 81. The holes 81 are blind as shown and are evenly circumferentially spaced about the center of rotation, namely the axis of the center pin 72. The holes 81 are near but spaced inboard of the peripheral surface 84 of the block 76. The number of sample holes 81 (40 in the example shown) is equal to the number of rotative steps taken by the turntable 17 in 360° of rotation and may be varied as desired. The diameter of the holes 81 is sufficient to permit free insertion and removal of the vials V from the holes 81 without excessive clearance. Minimizing the air space between the sides of the vials V and surrounding walls of the hole 81 enhances heat transfer therebetween to maintain the vials at the temperature of the block 76.

A tube 86 of insulating material forms a peripheral wall snugly surrounding the periphery of disk 74 and block 76 and extending above the top face of the latter. The tube 86 is fixed to the peripheral wall of block 76, preferably by a suitable adhesive.

A temperature control unit 91 (FIG. 4) is supported on the top central portion of the block 76 in good heat transfer relation therewith and includes a substantially circular insulating cover 92 extending radially outward to near the circumferential array of vial openings 81, as more fully described hereafter.

An insulative sample ring 96, here of insulative sheet material thinner than that of disk 74 and tube 86, rests removably on the top surface of block 76, snugly contacts the inside of the tube 86 and extends beneath the insulative cover 92. Holes 97 are circumferentially distributed around the ring 96 in coaxial relation with the sample holes 81 in block 76. The sample vials V are snugly received through the holes 97. The total depth of each pair of holes 97 and 81 is less than the height of the vials V to the extent required to permit a cap C on the vial V to be disposed close above the ring 96 with the vial V seated in the hole 81.

The top of insulative peripheral wall 86 extends at least up to the capped top of the vial V, the radial space between the peripheral wall 86 and central insulating cover 92 being sufficient to loosely admit the cap C. It will be seen that except for openings 97 in the ring 96, which openings preferably are snugly filled by the vials V, the surface of the massive block 76 is entirely enclosed in insulating material, at its bottom by insulative disk 74, at its periphery by insulating peripheral wall 86 and at its top by insulative sample ring 96 and the insulating cover 92 of the temperature control unit, all of which rotate with the block 76, base plate 71 and turntable 17. However, this leaves the tops or caps C of the vials V exposed.

To cover the tops of the vials, a sample cover unit 101 is fixed upon the base 16 and does not rotate with the sample block 76. The cover unit 101 (FIGS. 3 and 4) comprises a slotted support ring 109 carried by a diametrally opposed pair of inverted L-shaped brackets 103 and 104. The bottoms of the brackets 103 and 104 and releasably fixed by screws 106 to the sides of the base 16 and extend upward along the outside surface of the insulative peripheral wall 86. The tops of the brackets 103 and 104 form short, radially inwardly extending flanges 107 spaced above the vial caps C and top of the peripheral wall 86. The brackets 103 and 104 are of sheet metal. A flat slotted ring of sheet metal is fixed beneath the flanges 107 of the brackets 103 and 104, as by spot welding. The slotted ring 109 is thus fixed coaxially above the insulating peripheral wall 86 and sample holes 81 and loosely surrounds the temperature control unit 91.

The sample cover unit 101 further includes a slotted insulative ring 111 fixed, preferably by adhesive bonding, coaxially beneath the slotted sheet metal ring 109. Thus, the slotted insulating ring 111 is fixed with respect to the base 16 and against rotation with the sample block 76. The slotted insulating ring 111 closely overlies the insulating peripheral wall 86 and extends radially close to the insulating cover 92, but clears both to permit their rotation relative to the ring 111. Thus, the slotted insulating ring 111, throughout its major circumferential length, substantially closes the annular space 112 (FIG. 4) normally occupied by the tops of the vials V and, if provided, caps C, to minimize heat exchange thereby with the surrounding atmosphere.

The circumference of the insulating ring 111 is broken by a generally wedge-shaped, radially outwardly divergent slot 114 (FIGS. 3 and 6). The wedge-shaped slot 114 opens toward the bracket 27 of the probe carriage 23 and toward the mounting rod 47 of the sampling needle guide unit 46. As further seen in FIGS. 3, 5 and 6, the slot 114 permits the front end 53 of the guide arm 49 to enter snugly thereinto in its operative position wherein its funnel opening 54 coaxially overlies one of the holes 81 containing a vial next to be sampled, and such that the arm 49 lies close to the leftward edge of the slot 114. The diverging outer portion of the slot 114 also accommodates, near its rightward edge, the vertical leg 59 of probe bracket 27 with the carriage 23 in its above-described forward lower (sampling) position. The angular width of the slot 114 is kept narrow so that the slotted insulating ring 111 covers all of the openings 81 except the one located beneath the probe guide funnel 54.

The slotted sheet metal ring 109, as seen in FIGS. 3, 5 and 6, has a slot 117 which directly overlies the slot 114 and has substantially the same shape thereas except for a radially narrow tab 118 extending a rightwardly from the peripheral edge portion of the slot 117 to rest on the guide arm 49. Thus, the support of the rings 109 and 111 above the rotating peripheral wall 86 can be assisted by the adjustably fixed guide arm 49.

Figure 4:
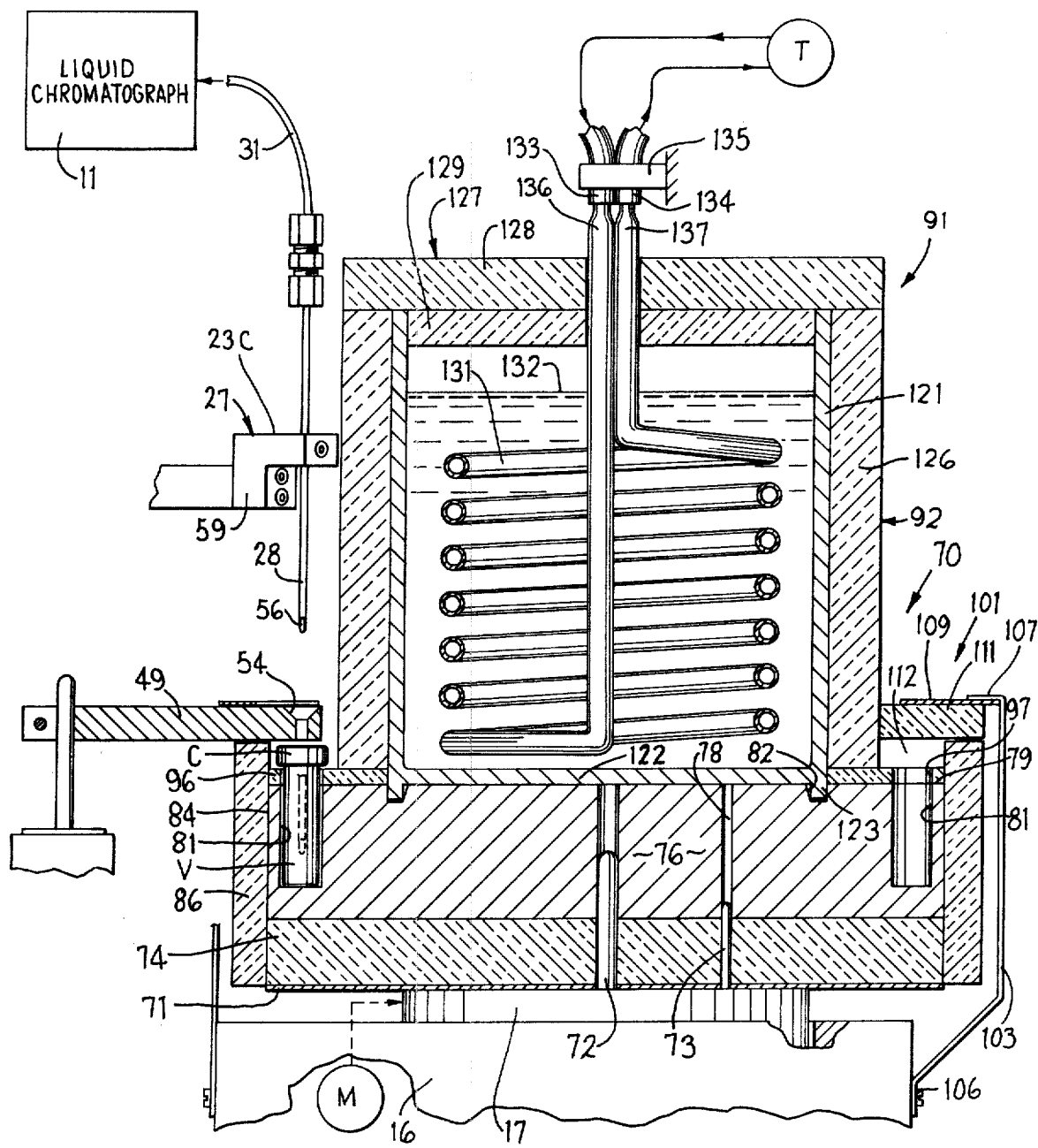
FIG. 4 is a partially schematic, enlarged cross-sectional view substantially taken on the line IV—IV of FIG. 3.

In the embodiment shown in FIGS. 2-4, the temperature control unit comprises a cylindrical bucket 121 of highly heat conductive material received snugly within the insulative sample ring 96 and having its bottom wall 122 resting in a large area contact on the top surface of the sample block 76. In the preferred embodiment shown, the bucket 121 is coaxially located upon the block 76 by reception of the depending peripheral rim 123 thereof in the coaxial annular groove 82 in block 76. The groove 82 assists both proper alignment and thermal contact of the bucket 121 and block 76. The insulating cover 92 includes a tubular insulating member 126 supported atop the inner edge portion of the insulating sample ring 96 and extending upwardly in snug fashion somewhat past the top of the bucket 121. The insulating cover 92 further includes an insulative cap 127, here with the cap plate 128 overlying the tubular member 126 and a bottom plate 129 snugly received in the open top of the bucket 121.

The temperature control unit 91 to the extent above described can be used to control sample temperature by filling of the bucket 121 with a controlled temperature liquid, for example a slush containing both liquid and frozen phases of a liquid, such as water, alcohol, etc., which will tend to maintain the bucket and hence the block 76 at the freezing temperature of the liquid.

Figure 7:
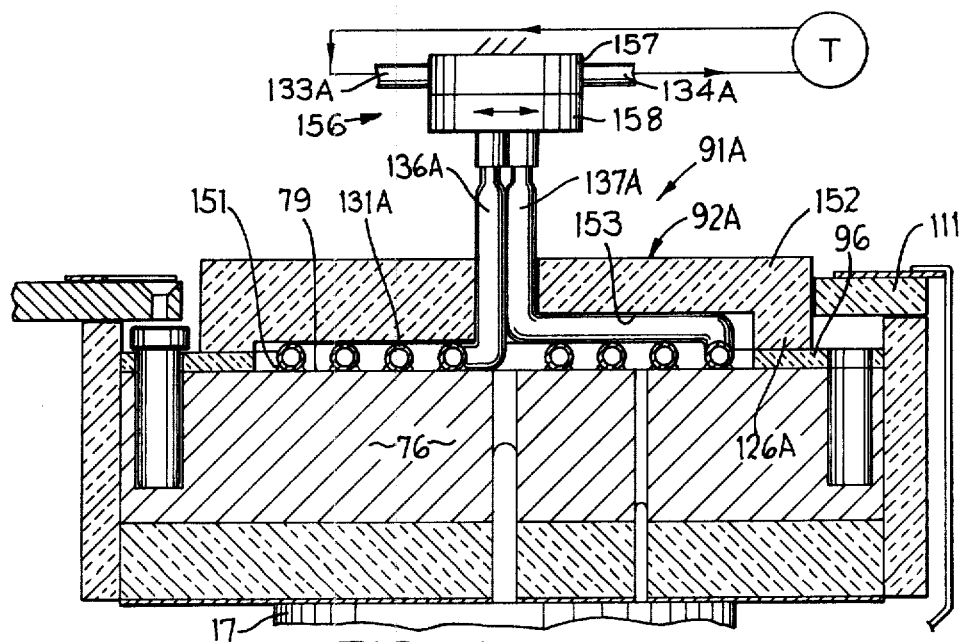
FIG. 7 is a fragmentary cross-sectional view similar to FIG. 4 but showing a modified temperature control means.

For closer temperature control or more flexible selection of desired sample temperature, the bucket 121 may contain a heat exchange coil 131 immersed in a heat exchange liquid generally indicated at 132, such as water or alcohol. The coil 131 may be of any desired form, here for example a substantially helical coil of copper or similar heat conductive tubing connected through flexible inlet and outlet fittings 133 and 134 to a conventional temperature control source of circulating heat transfer liquid schematically indicated at T. The ends 136 and 137 of the coil 131 are led up through a central opening in the cap 127 which may be separated from the coil by disconnection of the fittings 133 and 134. In the embodiment shown, the coil 131 is fixedly supported as schematically indicated at 135, with the bucket 121 and insulating cover 92 rotatable relative thereto. If desired, the coil 131 may rotate as well, and connect to the fixed fittings 133 and 134 through a conventional relative rotation fluid coupling, for example as shown in FIG. 7. The fixed support 135 is of any convenient type and is respositionable to allow disassembly of the apparatus including removal of the coil 131, and/or bucket 121 and/or the entire unit 91 from the turntable 17.

The sheet metal parts 71, 103, 104 and 109 are preferably of stainless steel and the block 76 and the bucket 121 are preferably of aluminum. The insulation elements 74, 86, 96, 126 and 128 are of material having chemical inertness, structural stability, and excellent insulating and vapor barrier properties, such as a resilient foam sheet material sold under the trademark "Armaflex" by the Armstrong Industrial Products Division, located at Lancaster, Pa. The adhesive used to mount the insulative tube 86 and split ring 11 may be Armstrong 520 adhesive, available from the same source. The center pin 72 is preferably of a heat insulative rigid plastic material, such as a fiber reinforced phenolic, rather than metal, to reduce heat flow between the base plate 71 and block 76.

OPERATION

While the operation of the apparatus will be apparent from the foregoing description, the following summary is provided for convenient reference.

With the sample cover unit 101 removed, vials V to be tested may be loaded into the plural holes 81 in the sample block 76 with the temperature controlled sample carrier 70 in place on the turntable 17 as in FIG. 4. Alternately, by moving the needle guide arm 49 to its dotted-line position of FIG. 3, moving the coil support bracket 135 out of the way, and disconnecting the coil ends 136 and 137 (or removing the coil 131 and/or bucket 121), the block 76 and associated insulation 74, 86 and 96 can be removed from the turntable 17 for loading with vials V at a remote location and, if desired, for storage at controlled temperature (as in a thermostatically controlled refrigerator or oven cabinet) until needed for testing. At that time, the apparatus is reinstalled on the turntable 17 in its condition seen in FIGS. 2-4, with the needle guide arm 49 swung into its solid-line operative position, the sample cover unit 101 reinstalled and the bucket 121 held at the desired temperature by filling with liquid 132 of desired temperature, alone or assisted by immersion therein of coil 131 connected to the fluid circulating, temperature controlled source T.

The temperature controlled sample carrier 70 may thus be loaded with test sample vials V and brought to desired test temperature while at a remote location by external means, or while on the turntable 17 of the automatic sampler by means of the temperature controlled contents of the bucket 121.

In any event, the contents of the bucket 121 hold the block 76 and hence the vials V at the desired test temperature throughout the sequential testing.

During testing, the sample vials V are brought sequentially into position for sample injection by clockwise stepped rotation of the turntable 17. Automated injection of the samples is accomplished by the automatic sampler 12 in the manner described in the above-referenced Smith and Beyer patents.

In one example, prepared samples of a solid material in a suitable solvent were thermostated at temperatures close to $-20°$ C. to prevent degradation of the solid material by the solvent. Adequate temperature control was obtained by using a water:methanol (75:25) slush.

However, it has been found that more precise temperature control can be achieved by circulating a thermostated fluid through the coil 131 immersed in a liquid in the bucket 121.

In further experiments, the long-term temperature control provided by the temperature controlled sample carrier 70 was studied at $0°$ C. and $-20°$ C. A pyrometer equipped with an iron-constantan thermocouple was used to monitor the temperature in the sample compartments (holes 81) with a precision of $\pm 0.1°$ C. Temperature fluctuations of $3°-4°$ were observed over a 2-3 hour period when the temperature was controlled by a slush in the bucket 121. The magnitude of these fluctuations was reduced by frequently adding small amounts of dry ice to the slush and stirring. On the other hand, circulation of a thermostated fluid (in one example methanol) through the coil 131 immersed in the bucket 121 was found to be substantially more convenient than the slush technique and also provided improved temperature control that was within the precision of the pyrometer, namely $\pm 0.1°$ C. The temperature controlled sample carrier 70 is considered to have application at least in the temperature range from $-40°$ C. to $+150°$ C.

MODIFICATION

The FIG. 7 embodiment is preferably similar to that above described with respect to FIGS. 1-6 except for the temperature control unit. More particularly, the modified temperature control unit 91A comprises a flat heat exchange coil 131A, for example a spiral coil, of heat conductive tubing having inlet and outlet ends 136A and 137A connected to a source T of temperature controlled heat exchange liquid. The flat coil 131A rests in wide area heat exchange contact with the top face 79 of the block 76 and is fixed thereto by any convenient thermally conductive means 151, such as welding or a thermally conductive adhesive.

The insulating cover 92A, overlying the coil 131A, comprises a flat plate 152 of insulative material extending radially out to a clearance fit with the inner periphery of the slotted insulating ring 111. If necessary the underface of the insulative plate 152 can be grooved, as at 153, to permit one end portion of the coil to be brought from the coil periphery back toward the center of the coil structure for connection to the temperature controlled liquid source T. Also, if desired, the radial extent of the coil 131 can be limited to permit the insulating plate 152 to be provided with a depending peripheral wall 126A supported on top of the inner portion of the insulative sample ring 96 in the manner of the lower end of the tubular insulative member 126 of FIG. 4.

A conventional relative rotation fluid coupling 156 comprises a fixed portion 157 and a rotatable portion 158 to continuously connect the coil ends 136A and 137A to the fittings 133A and 134A, respectively.

The apparatus of FIG. 7 operates substantially in the manner above discussed with respect to the apparatus of FIGS. 1-6, except that the block 76 and coil 131A are removable as a unit from the turntable 17 and the relative rotation coupling 156 is disconnectible from the coil and repositionable to permit removal of the block 76, its insulative cup, the coil 131A and the insulating cover 92A from the turntable.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A temperature controlled sample carrier apparatus, of the type having:
    a fixed base;
    a rotating sample rack having a circumferential array of upwardly facing sample holes adjacent the periphery thereof for receiving sample vials and orbiting same sequentially past a sampling station;
    means for supporting and rotatably driving said sample rack atop said fixed base;
    including the improvement wherein said rack comprises a solid block of heat conductive material and of substantially cylindrical form, the top surface of said block being substantially unbroken except for said sample vial receiving holes adjacent the periphery thereof and the thickness of said block corresponding substantially to the height of said vials such that said block forms a massive heat sink, and including;
    an insulative cup having a peripheral wall and bottom wall and snugly receiving said sample block therein for rotation therewith, said insulative cup peripheral wall extending above said sample block;
    temperature control means for carrying a controlled temperature fluid, said temperature control means being in heat conductive contact with said block and disposed radially inboard of said array of sample holes at the central portion of said block, at least a portion of said temperature control means extending above said block;
    insulative cover means overlying said temperature control means and the central portion of said block for rotation therewith;
    an insulative cover ring and means supporting same fixedly with respect to said base in close spaced relation above the upper end of said insulative cup peripheral wall, said insulative cover ring extending radially inward into close spaced relation with said insulative cover means for permitting rotation of said insulative cup and cover means with respect to said insulative cover ring while minimizing thermal losses from said sample block in the annular space above said sample holes;
    means defining a circumferentially narrow opening in said insulative cover ring for access to the upper ends of sequentially presented sample vials rotating past said opening with said sample block.

2. The apparatus of claim 1 including an insulative sample ring extending between said peripheral wall of said insulative cup and said insulative cover means and carried atop said sample block for rotation therewith, said insulative sample ring having axial holes therethrough in register with said sample holes in said sample block for insertion of said sample vials, said insulative sample ring underlying said insulative cover ring.

3. The apparatus of claim 1, including a sampler located adjacent said base in fixed relation thereto, said sampler including a carriage movable vertically as well as laterally toward and away from said sample block, said carriage supporting a probe for movement above said insulating cover ring to a location above said opening therein and then downwardly through said opening into a sample vial located thereunder.

4. The apparatus of claim 3, including a sampling probe guide comprising a support carried on said fixed base, a guide member extending from said support to a position above the peripheral portion of said sample block, said guide member having a vertical guide hole therethrough for receiving the lower end of said probe and guiding same downward into engagement with a sample vial therebeneath, said opening in said cover ring comprising a slot extending from the outer to the inner periphery of said cover ring, said guide member extending into said slot, the edges of said slot being close adjacent said guide member such that said cover ring covers substantially all of said vial openings in said sample block except for the one to be sampled by said probe at any given time.

5. The apparatus of claim 1, in which said means fixedly supporting said insulating cover ring on said base comprise an annular sample cover overlying and pendently supporting said insulative cover ring and provided with an opening overlying said circumferentially narrow opening in said insulative cover ring, and support brackets releasably fixed to said fixed base and upstanding therefrom into fixed supporting relation with said annular sample cover.

6. In a temperature controlled sample carrier apparatus, of the type having:
    a fixed base;
    a rotating sample rack having an array of upwardly facing sample holes for receiving sample vials and moving same sequentially past a sampling station;
    means for supporting and movably driving said sample rack atop said fixed base;
    the improvement wherein said rack comprises a solid block of heat conductive material, the top surface of said block being substantially unbroken except for said sample vial receiving holes and the thickness of said block corresponding substantially to the height of said vials such that said block forms a massive heat sink, and including;
means for insulating the bottom and side surfaces of said sample block;
temperature control means in heat conductive contact with said block near said array of sample holes;
insulative cover means covering said temperature control means;
means fixed with respect to said base for insulating against heat transfer above the portion of said block containing said sample vial receiving holes, between said bottom and side insulating means and said insulative cover means, said fixed means permitting access to a sample vial in said block, in which said temperature control means comprises a thermostat bucket coaxially removably supported on said rotating sample block, said thermostat bucket being of thermally conductive material, said thermostat bucket having a bottom wall in wide area heat transmitting contact with the top of said sample block, the periphery of said bucket being close spaced radially inboard from said sample holes;
said insulative cover means comprising a bucket insulating cylinder snugly surrounding said thermostat bucket and a removable insulative bucket cover atop said bucket insulating cylinder and bucket.

7. The apparatus of claim 6, including means defining an annular groove in the top of said sample block, the peripheral wall of said bucket extending downward somewhat past the bottom wall of said bucket to define a downward facing annular flange, said annular flange being removably received in said annular groove for coaxially centering said bucket on said rotating sample block, the depth of said groove somewhat exceeding the axial extent of said annular flange to permit the bottom of said bucket to rest snugly on the portion of the top of said sample block inboard of said annular groove and flange.

8. The apparatus of claim 6, in which said bucket is liquid-tight and capable of containing a liquid bath of desired temperature and, through its contact with said sample block, maintaining sample vials in said sample block substantially at said temperature.

9. The apparatus of claim 8, including a heat exchanger comprising a hollow tubular member of heat transferring material formed in a coil and connected to a flowing source of thermostatically temperature controlled fluid, said coil being immersed in a heat transfer liquid in said bucket for maintaining said sample block and sample vials therein substantially at the temperature of said thermostatically controlled source.

10. The apparatus of claim 9 including liquid conduits connected to said coil and extending through said insulative bucket cover.

11. The apparatus of claim 1 in which said temperature control means comprises a hollow tubular member of heat transferring material formed in a flat coil fixed in heat conducting relation to the top of said block, and having ends extending away from said block for connection to a flowing source of thermostatically temperature controlled fluid, insulative said cover means comprising a cover plate overlying said coil and through which said ends extend, said insulative cover plate having a central portion recessed at its underside for receiving said coil, and an insulative sample ring atop said sample block for rotation therewith, said insulative sample ring snugly engaging the peripheral wall of said insulative cup and extending across the holes in the sample block for snugly engaging the peripheral portion of said insulative cover plate, said insulative sample ring having holes for insertion of said sample vials into said sample block, said fixed insulative cover ring bridging the annular gap between the rotating insulative cover plate and cup peripheral wall with said holes in said rotating insulative sample ring spaced therebelow.

12. A method for conducting automatic liquid chromatography testing of a series of liquid samples at a test temperature different from room temperature, comprising the steps of:
loading a plurality of vials each containing a liquid test sample into corresponding holes circumferentially distributed near the periphery in the top of a massive cylindrical block of heat conductive metal;
limiting heat transfer between the block and the atmosphere by insulating the side and bottom surfaces of said block;
contacting the major central portion of said top of said block in heat transfer relation with a hollow member carrying a temperature controlled fluid and limiting heat transfer between said member and the atmosphere by enclosing said hollow member at its top and sides with insulative material;
supporting said block and its bottom and side insulation for stepwise rotation past a sampling station;
supporting an insulative slotted ring in fixed relation with respect to the sampling station to insulatively cover the tops of the vials while permitting stepwise rotation of said block and vials therebeneath and circumferentially locating a substantially radial slot in said insulative ring adjacent said sampling station, with said slot being circumferentially wide enough to permit sampling access to one vial at a time;
maintaining a controlled temperature fluid in said hollow member atop said block and thereby maintaining said block and the vials carried thereby at a desired temperature;
rotatably indexing said block past said sampling station while synchronously presenting a sample probe through said slot to successively presented sample vials carried by said block.

13. In an automatic sampler, usable for liquid chromatography and the like, the combination comprising:
a fixed base;
a rotating sample rack having a circumferential array of upwardly facing sample holes adjacent the periphery thereof for receiving sample vials and orbiting same sequentially past a sampling station;
means for supporting and driving said sample rack for stepped rotation atop said fixed base;
means supporting a sampling probe for movement into and out of a sampling position at a point along the orbit of said vials in synchronism with said stepped rotation;
the improvement wherein said rack comprises a massive heat sink in the form of a substantially cylindrical solid block of heat conductive material having a top surface broken by said sample vial receiving holes adjacent the periphery thereof and a thickness of said block exceeding the height of said vial receiving holes, and including;

means for insulating the bottom and side surfaces of said sample block;

temperature control means in heat conductive contact with said block and disposed radially inboard of said array of sample holes at the central portion of said block;

insulative cover means overlying said temperature control means at the central portion of said block for rotation therewith;

insulative means supported fixedly with respect to said base above said block and extending between said rotating side insulating means and said insulative cover means in the annular space above said sample holes for permitting rotation of said side insulating means and insulative cover means with respect thereto while minimizing thermal exchange between the atmosphere and said sample block in the annular space above said sample holes, said fixed means permitting access to a sample vial in said sample block.

14. In a temperature controlled sample carrier apparatus, of the type having:

a fixed base;

a movable sample rack having an array of upwardly facing sample holes for receiving sample vials and moving same sequentially past a sampling station;

means for supporting and movably driving said sample rack atop said fixed base;

the improvement wherein said rack comprises a movable solid block of heat conductive material, the top surface of said block being substantially unbroken except for said sample vial receiving holes and the thickness of said block corresponding substantially to the height of said vials such that said block forms a massive heat sink, and including;

means movable with said sample block for insulating the bottom and side surfaces of said sample block;

temperature control means in heat conductive contact with the top portion of said block to one side of said array of sample holes and at least in part movable therewith;

insulative cover means movable with said sample block and overlying said temperature control means, said holes being arranged in a row in said block, said insulative cover means and side insulating means flanking closely the space above said holes and forming a narrow gap corresponding closely to the width of said holes;

an insulative strip fixed with respect to said base for insulating against heat transfer into or out of the gap above the portion of said block containing said sample vial receiving holes, said fixed insulative strip closely confronting the relatively moving surfaces of said movable side insulating means and said movable insulative cover means on opposite sides of said gap, said fixed insulative strip permitting access to a sample vial in said block.

* * * * *